United States Patent [19]

Rogachev et al.

[11] 4,072,895
[45] Feb. 7, 1978

[54] EDDY CURRENT CONVERTER FOR NON-DESTRUCTIVE TESTING OF ELECTRICALLY CONDUCTING COATING IN HOLES OF PRINTED CIRCUIT BOARDS

[76] Inventors: Viktor Igorevich Rogachev, Jurievsky pereulok, 22, korpus 2, kv.55.; Vasily Vasilievich Sukhorukov, 2, Vladimirskaya, 50, korpus 2, kv.51.; Petr Nikolaevich Shkatov, Lefortovsky val, 7/6, korpus 4, kv.69., all of Moscow, U.S.S.R.

[21] Appl. No.: 652,891

[22] Filed: Jan. 27, 1976

[51] Int. Cl.² .................................................. G01R 33/12
[52] U.S. Cl. .................................... 324/238; 324/237
[58] Field of Search ................... 324/34 R, 34 TK, 37, 324/40

[56] References Cited

U.S. PATENT DOCUMENTS

| | | | |
|---|---|---|---|
| 2,844,787 | 7/1958 | McCann | 324/37 |
| 3,495,166 | 2/1970 | Lorenzi et al. | 324/40 |
| 3,840,802 | 10/1974 | Anthony | 324/40 |

FOREIGN PATENT DOCUMENTS

| | | | |
|---|---|---|---|
| 650,012 | 10/1962 | Canada | 324/37 |
| 2,061,708 | 7/1971 | Germany | 324/34 TR |

*Primary Examiner*—Robert J. Corcoran
*Attorney, Agent, or Firm*—Haseltine, Lake & Waters

[57] ABSTRACT

The proposed eddy current converter for non-destructive testing of electrically conductive coating in holes of printed circuit boards comprises a cylindrical frame enveloped by an exciting winding and a measuring winding and inserted into a hole of a printed circuit board being tested. The coils of the exciting and measuring windings extend along the generatrices of the cylindrical frame.

With the use of the proposed converter, the testing accuracy is independent of the parameters of respective contact areas of a hole being tested. The converter of the present invention is sensitive to the most undesired flaws like transversely extending cracks.

3 Claims, 5 Drawing Figures

EDDY CURRENT CONVERTER FOR NON-DESTRUCTIVE TESTING OF ELECTRICALLY CONDUCTING COATING IN HOLES OF PRINTED CIRCUIT BOARDS

The present invention relates to means for non-destructive testing of manufactured articles and, more particularly, to an eddy current converter for non-destructive testing of electrically conducting coating in holes of printed circuit boards.

The invention is applicable in general engineering, instrument making, nuclear engineering, computers and data processing equipment, and radioelectronics for testing electrically conducting hole walls, the internal surfaces of tubes, electrically conducting coating in holes of printed circuit boards, and other hollow articles having electrically conducting internal surfaces.

Quality testing of electrically conducting coating in holes of printed circuit boards is widely practiced today as an important means to raise the reliability of a host of sophisticated radioelectronic devices. The latter include all types of data processing and measuring systems, computers, means of communication etc. At present, printed circuit boards are the only means of electrical connection between components of the above-mentioned devices and systems. The reliability of connection is largely determined by the quality of metallization of printed circuit board holes. Experiments show that if a rated metallization thickness of 20 to 25 mu is reduced to 15 mu, some 50 percent of connections become faulty; when the thickness is reduced to 7 mu, a break in the connection is sooner or later unavoidable, as the coating is destroyed by oxidation, as well as mechanical and temperature effects (impacts, vibration, etc.).

Of particular importance is metallization of holes in multilayer printed wiring boards which find an increasingly wide application in radioelectronics today. In such boards, all electrical connections between layers are only effected by metallizing the holes. A break in the connection due to faulty metallization can be detected in the course of an electric test of the printed circuit board; yet it is impossible to detect a reduction in the thickness of the electrically conducting coating below a permissible limit in the course of such a test. Defects of this type are hard to detect, but they show themselves in the course of operation of a critical and costly piece of equipment into which the printed circuit board is incorporated.

Normally, holes of printed circuit boards have a diameter of 0.5 to 2 mm with the board thickness between 0.5 and 3 mm. The small size of the holes makes the testing extremely difficult. In addition, articles to be tested are of complex configurations. If the internal surface of a tubular article is provided with a coating, adjoining said coating at its butt ends are contact areas which serve for the assembly of components. According to technological requirements, the thickness of such contact areas may vary within broad limits. Adjoining the coating in multilayer printed circuit boards are also flat conductors of individual layers.

There are different methods of testing the quality of metallization of holes of printed circuit boards, which include the optical, electrical, contact, radiation, thermal, eddy current and other methods. Optical testing is disadvantageous in its subjectivity and limited efficiency. This method enables one to assess the quality of the coating's surface, but does not make it possible to measure the thickness of the coating. The radiation method requires meticulous calibration of the instrument; in addition, its efficiency is limited (the measuring time amounts to 1 minute per hole); finally, this method is only fit for measuring the coating thickness in holes with a diameter of more than 0.85 mm. The method also requires radiation shielding, which limits its industrial application.

The thermal (infrared) testing method calls for sophisticated and expensive equipment and is employed for detecting flaws in the coating of holes, such as uncoated areas, impurities, etc.

At present, research is underway on using eddy currents for testing the quality of metallization in holes of printed circuit boards. The latter method is advantageous over those mentioned above in that it provides for contactless testing of the quality of electrically conducting coating in holes of printed circuit boards. In addition, the latter method is highly efficient, is carried out with the aid of simple devices, and makes unnecessary stringent safety measures.

Widely known in the art are converters for non-destructive quality testing of internal surfaces of hollow, electrically conducting articles (cf. "Nerazrushayushchiye ispytaniya" ("Non-Destructive Testing"), ed. by R. McMaster, Part II, Moscow, Energhia Publishers, 1965).

A converter of this type comprises a cylinder-shaped frame coaxially enveloped by one or more windings and placed in a hole of an article being tested.

There exists a parametrical version of such a converter, which makes it possible to evaluate the parameters of an article being tested by following changes in the complex impedance of the winding which serves to induce eddy currents in the article being tested. Another version of this type of converter is the transformer version, when information on an article being tested is carried by the e.m.f. of another winding which is a measuring winding. A transformer converter may be differential. In this case, information on a deviation from rated values of parameters of an object being tested is provided by the difference of the electromotive forces of two measuring windings arranged inside an article being tested and a control article, respectively.

The cylindrical frame with the windings is inserted into a hole being tested so that their axes are matched. The exciting winding, which is connected to an a.c. generator, induces circular eddy currents in the article being tested. The total electromagnetic field, which is determined by the exciting field and that of circulating eddy currents, affects the resistance of the exciting winding and the e.m.f. of the measuring windings. Information in the form of changes in the impedance or e.m.f. of the windings is processed by electronic devices and registered by measuring instruments.

The known converter does not provide for high accuracy of testing the quality of metallization of holes of printed circuit boards. This is due to the fact that the eddy currents induced by said converter circulate not only in the coating of a hole being tested, but also in contact areas and layers of the multilayer printed circuit board. Hence, variations in the parameters of contact areas and layers, for example, variations in their thickness, largely account for measuring errors. Besides, the converter under review is insensitive to the worst flaws like transversely extending cracks.

It is an object of the present invention to raise the accuracy of testing electrically conducting coating in holes of printed circuit boards.

The aforesaid object is attained by providing an eddy current converter for non-destructive testing of electrically conducting coating in holes of printed circuit boards, comprising a cylindrical frame enveloped by an exciting winding and a measuring winding and placed in a hole of a printed circuit board being tested, the coils of the exciting and measuring windings extending along the generatrices of the cylindrical frame.

In order to reduce axial displacement of the converter relative to an article being tested, it is expedient that the length of the cylindrical frame with the windings should be at least 1.2 of the thickness of the printed circuit board.

The proposed converter has a number of advantages over the known type of converter.

The proposed converter raises the accuracy of the testing, because the converter's signal is practically independent of variations in the parameters of respective contact areas; likewise, this signal is not affected by possible axial displacement of the converter during measurements.

Another advantage of the converter according to the invention resides in the fact that flaws like transversely extending cracks, which are the worst defects of coating, considerably affect the magnitude of the useful signal.

The latter is due to the fact that the proposed converter induces eddy currents directed along the hole's walls. As a result, the length of the eddy current circuit enveloping a contact area is small, as compared to that part of the circuit which is connected to the coating tube. Minor axial displacements of the converter relative to an article being tested, which are possible in the course of testing, do not affect the converter's signal because the converter's frame with the windings is longer than the coating tube.

This makes it possible to use the proposed converter for detecting coating flaws.

Other objects and advantages of the present invention will become more apparent from the following detailed description of exemplary embodiments thereof taken in conjunction with the accompanying drawings, wherein.

Figure 1:
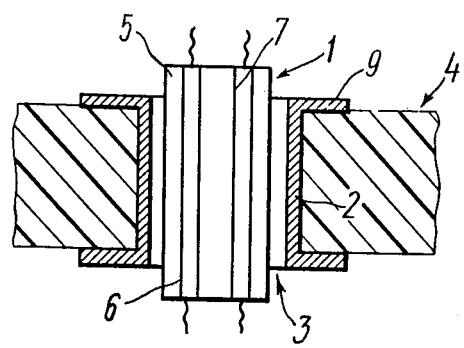
FIG. 1 is a general schematic view of a parametrical version of an eddy current converter for non-destructive testing of the quality of electrically conducting coating in holes of printed circuit boards, inserted into a hole being tested, in accordance with the invention.

Referring now to the attached drawings, the proposed eddy current converter 1 (FIG. 1) for non-destructive testing of the quality of electrically conducting coating 2 in a hole 3 of a printed circuit board 4 comprises a cylindrical frame 5 with coils of a winding 6 extending along its generatrices.

Figure 2:
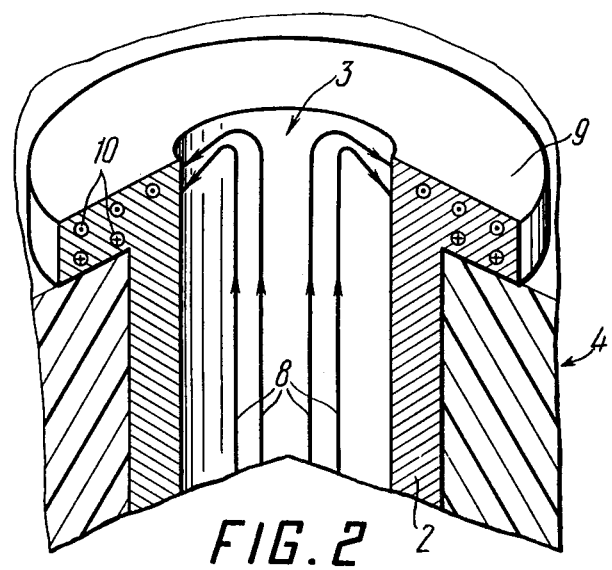
FIG. 2 shows the distribution of eddy currents induced by the above-mentioned converter in the coating being tested and contact areas.

The exciting winding 6 serves to induce eddy currents 8 (FIG. 2) in the electrically conducting coating 2 (FIG. 1) and a contact area 9. A measuring winding 7 is intended for registering the electromotive force induced in its coils and depending upon the parameters of the coating 2.

Figure 3:
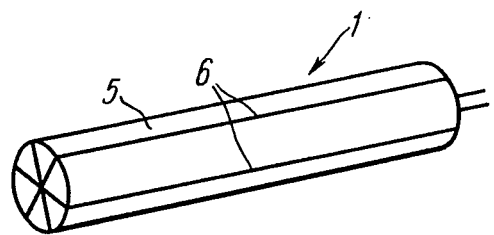
FIG. 3 is a general view of a parametrical version of an eddy current converter for non-destructive testing of the quality of electrically conducting coating in holes of printed circuit boards, in accordance with the invention.

The converter 1 may have only one winding 6 (FIG. 3) which serves both as the exciting and measuring winding. Said winding 6 serves to induce eddy currents in the coating 2 and monitor changes in its own resistance which depends upon the parameters of the coating 2.

Figure 4:
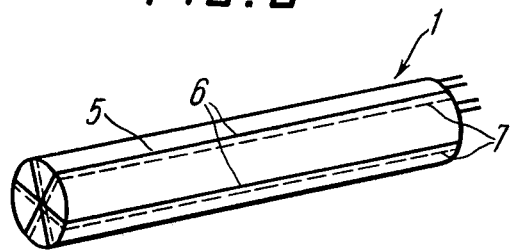
FIG. 4 is a general view of a transformer version of an eddy current converter for non-destructive testing of the quality of electrically conducting coating in holes of printed circuit boards with the coils of the exciting and measuring windings laid in the same slots, in accordance with the invention.
Figure 5:
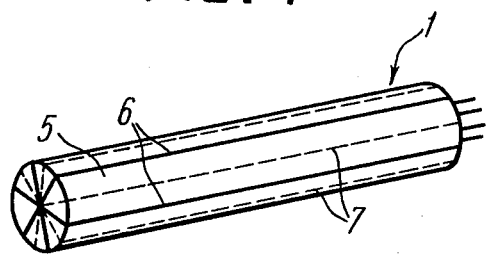
FIG. 5 is a general view of a transformer version of an eddy current converter for non-destructive testing of the quality of electrically conducting coating in holes of printed circit boards with slots for the exciting winding and those for the measuring winding being displaced relative to each other, in accordance with the invention.

The converter 1 may be constructed as the cylindrical frame 5 enveloped by the windings 6 and 7, in which case the windings 6 and 7 may be arranged in different ways on the frame 5. The measuring winding 7 is either laid in the same slots as the exciting winding 6, as shown in FIG. 4, or is laid in slots specially provided for said measuring winding 7 (FIG. 5).

In the course of measurements, axial displacements of the converter 1 relative to the coating 2 being tested amount, as a rule, to about 0.1 mm. Such displacements are due to inaccuracies in holding said converter 1 in place. For that reason, the length of the cylindrical frame 5 is more than 1.2 the thickness of the printed circuit board 4 being tested, which reduces measurement errors due to possible axial displacements of the converter 1 with respect to the hole 3 being tested.

For example, if the printed circuit board is 1 mm thick, the length of the cylindrical frame 5 with its windings is more than 1.2 mm.

The proposed eddy current converter 1 (FIG. 1) for non-destructive testing of the quality of the coating 2 in the hole 3 of the printed circuit board 4 operates as follows.

The cylindrical frame 5 with the winding 6 is introduced into the hole 3 being tested and arranged so that the axes of the frame 5 and the hole 3 are matched. Alternating current is passed through the winding 6 and produces a variable magnetic field. Said field envelops the electrically conducting coating 2 and induces eddy currents therein. Due to the fact that the coils of the winding 6 extend along the axis of the frame 5, the variable magnetic field has no axial component in the testing zone; hence, the eddy currents circulate in the coating 2 along the axis of the hole 3, and their circuit is closed at its butt ends. As a result, the length of the circuit of the eddy currents 8 (FIG. 2) is proportional to the product of the diameter of the hole being tested by the thickness of the printed circuit board 4. Eddy currents 10 are induced in the contact areas 9. Said eddy currents 10 run parallel to the surface of the printed circuit board 4, and their circuit is closed at the upper and lower surfaces of the contact areas 9. The length of the eddy current circuits in the contact arms 9 is proportional to the product of their thickness by the diameter of the hole 3 being tested. It must be noted that the frequency of the exciting current is selected so that the penetration depth of an electromagnetic field wave should be about the thickness of the coating 2 being tested. Thus, the density of the eddy current 10 circulating in the outer layers of the contact area is rather small. At the same time, the value of a possible variation in the thickness of the contact area 9 is scores of times less than the thickness of the printed circuit board 4. Hence, variations in the parameters of the contact area 9 cannot considerably affect the useful signal of the converter.

The eddy currents 10 circulating in the coating 2 depend upon the thickness of said coating 2 and the presence therein of longitudinally and transversely extending flaws. Hence, the converter 1 can be used both for measuring the thickness of the coating 2 and detecting flaws therein.

Due to the fact that the length of the cylindrical frame 5 is more than 1.2 of the thickness of the printed circuit board 4 being tested, axial displacements of the converter 1 relative to the hole 3 being tested can practically be ignored.

A parametrical version (FIGS. 1 and 3) of the proposed converter 1 may be placed in the circuit of a self-excited oscillator or a resonance amplifier (as described in "Nerazrushayushchiye ispytaniya" ("Non-Destructive Testing"), ed. by R. McMaster, Part II, Energhia Publishers, Moscow, 1965). In this case, changes in the oscillation amplitude and frequency of the self-exciting oscillator, or changes in the amplitude and phase of the output voltage of the resonance amplifier provide information on the parameters of the coating 2 in the hole 3 of the printed circuit board 4.

In the transformer version (FIGS. 4 and 5) of the proposed converter, the exciting winding 6 is connected to an a.c. generator (not shown), whereas the measuring winding 7 is connected to an amplifier (not shown). In the latter case, the amplitude and phase of the output voltage of the amplifier provide information on the thickness of the metallization layer and the presence of flaws therein.

What is claimed is:

1. An eddy current converter for non-destructive testing of electrically conducting coating in holes of printed circuit boards, comprising:

a cylindrical frame inserted in a hole being tested of a printed circuit board;

a winding enveloping said cylindrical frame, said winding being inserted for testing together with said cylindrical frame into said hole of the printed circuit board being tested, said winding when energized inducing eddy currents in said coating and sensing the induced eddy currents; and conductors of said winding extending in an axial direction all over the surface of said cylindrical frame the axial length of the conductors and cylinder being greater than the depth of the holes of the printed circuit boards.

2. An eddy current converter for non-destructive testing of electrically conducting coating in holes of printed circuit boards, comprising:

a cylindrical frame inserted into a hole being tested of a printed circuit board;

an exciting winding with wires enveloping said cylindrical frame and inserted with said cylindrical frame in said hole of the printed circuit board being tested, said winding when energized inducing eddy currents on said coating;

conductors of said exciting winding extending in an axial direction all over the surface of said cylindrical frame;

a measuring winding with wires enveloping said cylindrical frame and inserted with said cylindrical frame in said hole of the printed circuit board being tested for sensing the induced eddy currents;

conductors of said measuring winding extending in an axial direction all over the surface of said cylindrical frame, the axial length of the conductors and cylinder being greater than the depth of the hole of the printed circuit board.

3. An eddy current converter as claimed in claim 2, wherein the length of said wires of said exciting and measuring windings extending all over the surface of said cylindrical frame exceed 1.2 the thickness of said printed circuit board.

* * * * *